(12) United States Patent
Roussev et al.

(10) Patent No.: US 9,696,207 B2
(45) Date of Patent: *Jul. 4, 2017

(54) METHOD OF ENHANCING CONTRAST IN PRISM COUPLING MEASUREMENTS OF STRESS

(71) Applicant: Corning Incorporated, Corning, NY (US)

(72) Inventors: Rostislav Vatchev Roussev, Painted Post, NY (US); Emily Elizabeth Young, Erin, NY (US)

(73) Assignee: Corning Incorporated, Corning, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/691,778

(22) Filed: Apr. 21, 2015

(65) Prior Publication Data

US 2015/0308897 A1    Oct. 29, 2015

Related U.S. Application Data

(60) Provisional application No. 61/983,151, filed on Apr. 23, 2014.

(51) Int. Cl.
*G01N 21/55* (2014.01)
*G01J 3/42* (2006.01)
(Continued)

(52) U.S. Cl.
CPC ............ *G01J 3/42* (2013.01); *G01J 3/0205* (2013.01); *G01J 3/0229* (2013.01); *G01L 1/241* (2013.01);
(Continued)

(58) Field of Classification Search
CPC .... G01N 21/00; G01N 33/00; G01N 21/4133; G01N 21/552; G01J 3/00; G01J 3/0205; G02B 21/00; G02B 27/00; G02F 1/00
(Continued)

(56) References Cited

U.S. PATENT DOCUMENTS 3,308,394 A    3/1967    Snitzer et al.
3,433,611 A    3/1969    Saunders et al.
(Continued)

FOREIGN PATENT DOCUMENTS

GB    967641    8/1964
JP    5531944    3/1980
(Continued)

OTHER PUBLICATIONS

Kishii, Toru; "Surface Stress Meters Utilising the Optical Waveguide Effect of Chemically Tempered Glass"; Optics and Lasers in Engineering 4 (1983); pp. 25-38.
(Continued)

*Primary Examiner* — Tarifur Chowdhury
*Assistant Examiner* — Isiaka Akanbi
(74) *Attorney, Agent, or Firm* — Kevin M. Johnson

(57) ABSTRACT

A method and apparatus for improving contrast in prism coupling measurements of waveguide mode spectra, wherein the measured waveguide sample has a surface region of rapidly decreasing index, characterized with normalized slope $$\left|\frac{\lambda}{n}\frac{dn}{dz}\right| > 0.0004.$$

An opaque light-blocking element is placed in the portion of the light beam closest to the plane of the contact between prism and measured sample, on the input side, output side or both sides of the prism. The light blocking element prevents light from the light source to reach a portion of the length of the prism-sample coupling interface along the optical path, prevents light reflected from a portion of the aforementioned length to reach the detector, or both when input and output light-blocking elements are used.

18 Claims, 11 Drawing Sheets

(51) Int. Cl.
  *G01J 3/02* (2006.01)
  *G01L 1/24* (2006.01)
  *G01N 21/552* (2014.01)
  *G01N 21/41* (2006.01)

(52) U.S. Cl.
  CPC .......... *G01L 1/242* (2013.01); *G01N 21/4133* (2013.01); *G01N 21/552* (2013.01); *G01N 2021/4166* (2013.01)

(58) Field of Classification Search
  USPC ............................ 356/445, 32, 451, 364, 440
  See application file for complete search history.

(56) References Cited

U.S. PATENT DOCUMENTS

| | | | |
|---|---|---|---|
| 3,873,209 | A | 3/1975 | Schinke et al. |
| 3,883,221 | A | 5/1975 | Rigrod |
| 4,207,000 | A | 6/1980 | Miller |
| 4,353,649 | A | 10/1982 | Kishii |
| 4,637,684 | A | 1/1987 | Tomita et al. |
| 4,655,589 | A | 4/1987 | Cestaro et al. |
| 5,164,589 | A * | 11/1992 | Sjodin ................ G01N 21/552 250/227.24 |
| 5,446,534 | A * | 8/1995 | Goldman ............. G01J 3/0259 356/128 |
| 5,953,125 | A | 9/1999 | de Groot |
| 6,459,492 | B1 | 10/2002 | Hercher |
| 6,731,388 | B1 | 5/2004 | Simon et al. |
| 7,193,719 | B2 * | 3/2007 | Meehan ............... G01N 21/553 356/445 |
| 7,701,529 | B2 | 4/2010 | Kogure et al. |
| 8,281,510 | B2 | 10/2012 | Yoshimura et al. |
| 8,957,374 | B2 | 2/2015 | Liu et al. |
| 9,109,881 | B2 | 8/2015 | Roussev et al. |
| 9,140,534 | B2 | 9/2015 | Manlay |
| 9,140,543 | B1 | 9/2015 | Allan et al. |
| 2010/0028607 | A1 | 2/2010 | Lee et al. |
| 2012/0106164 | A1 | 5/2012 | Michaelis et al. |
| 2012/0257387 | A1 | 10/2012 | Kuchibhotla et al. |
| 2014/0092377 | A1 | 4/2014 | Liu et al. |
| 2014/0118740 | A1 * | 5/2014 | Fontaine ................ G01M 11/30 356/364 |
| 2014/0368808 | A1 | 12/2014 | Roussev et al. |
| 2015/0066393 | A1 | 3/2015 | Liu et al. |
| 2015/0116713 | A1 | 4/2015 | Roussev et al. |
| 2015/0338308 | A1 | 11/2015 | Li et al. |

FOREIGN PATENT DOCUMENTS

| | | |
|---|---|---|
| JP | 57157130 | 9/1982 |
| JP | 4310836 | 11/1992 |
| JP | 11281501 | 10/1999 |
| JP | 2002131224 | 5/2002 |

OTHER PUBLICATIONS

Tien et al.; "Theory of Prism-Film Coupler and Thin-Film Light Guides"; Journal of the Optical Society of America, vol. 60, No. 10 (Oct. 1970); pp. 1325-1337.

Ulrich et al.; "Measurement of Thin Film Parameters with a Prism Coupler"; Applied Optics, vol. 12, No. 12, (Dec. 1973); pp. 2901-2908.

R. Ulrich; "Theory of the Prism-Film Coupler by Plane-Wave Analysis"; Journal of the Optical Society of America, vol. 60, No. 10 (Oct. 1970); pp. 1337-1350.

Agan et al; "Stress effects in prism coupling measurements of thin polymer films"; Appl.Phys. A 80, 341-345 (2005).

Surface Stress Meter FSM-60 Manual, Orihara Industrial Co., Aug. 18, 2008.

Surface Stress Meter FSM-6000 Manual, Orihara Industrial Co., Aug. 18, 20018.

Kishii; "Surface Stress Meters Utilizing the Optical Waveguide Effect of Chemically Tempered Glasses"; Optics and Lasers in Engineering, 4 (1983) 25-38.

Metricon 2010 manual, Metricon corporation, Dec. 30, 2013.

Rau et al; "Prism coupled Terahertz waveguide sensor"; Applied Physics Letters, 86, 211119 (2005).

Tien, "Light waves in thin films and integrated optics", Applied Optics 10, p. 2395 (1971).

Tien et al;, "Theory of Prism-Film Coupler and Thin-Film Light Guides", Journal of the Optical Society of America 60, p. 1325 (1970).

Ulrich et al; "Measurement of Thin Film Parameters with a Prism Coupler"; Applied Optics, Dec. 1973, vol. 12, 2901-2908.

Ulrich; "Theory of the Prism-Film Coupler by Plane-Wave Analysis"; Journal of the Optical Society of America, vol. 60, No. 10 Oct. 1970.

Zernike et al,; "Improved Version of the Evanescent-Wave Coupler", IEEE Journal of Quantum Electronics, Sep. 1970, pp. 577-578.

Brandenburg, "Stress in Ion-Exchanged Glass Waveguides," Journal of LightwaveTechnology, vol. LT-4, No. 10, Oct. 1986, pp. 1580-1593.

Chiang et al; "Refractive-Index Profiling of Buried Planar Waveguides by an Inverse Wentzel-Kramer-Brillouin Method"; Journal of Lightwave Technology, IEEE, vol. 26, No. 11, Jun. 1, 2008 pp. 1367-1373.

Chiang et al; "Refractive-Index Profiling of Graded-Index Planar Waveguides From Effective Indexes Measured With Different External Refractive Indexes"; Journal of Lightwave Technology, IEEE, vol. 18, No. 10, Oct. 1, 2000 p. 1414 and 1416.

International Search Report and Written Opinion of the International Searching Authority; PCT/US15/26633; Mailed Jul. 30, 2015.

International Search Report and Written Opinion of the International Searching Authority; PCT/US2014/062370; Mailed Feb. 9, 2015.

Invitation to Pay Additional Fees; PCT/US2015/066022; Mailed Apr. 5, 2016.

McRae et al; "The measurement of compression stress in eggshells"; Journal of Agricultrual Engineering Research, vol. 14, No. 1, Mar. 1, 1969.

International Search Report and Written Opinion of the International Searching Authority; PCT/US2014/053069; Mailed Dec. 9, 2014.

Pelletier et al; "Optical characterization of thin films by guided waves"; Applied Optics; vol. 28, No. 14, Jul. 1989 pp. 2918-2924.

Pitt et al; "Lightguiding in Langmuir-Blodgett Films"; Thin Solid Films, vol. 68, No. 1 May 1, 1980 p. 114.

Surface Stress Meter FSM-6000 Manual, Orihara Industrial Co., Aug. 18, 2008.

* cited by examiner

METHOD OF ENHANCING CONTRAST IN PRISM COUPLING MEASUREMENTS OF STRESS

This application claims the benefit of priority under 35 U.S.C. §119 of U.S. Provisional Application Ser. No. 61/983,151, filed on Apr. 23, 2014, the content of which is relied upon and incorporated herein by reference in its entirety.

BACKGROUND

Nondestructive stress measurements through prism coupling have great importance for quality control in manufacturing of chemically strengthened cover glass for portable electronic devices.

Some chemically strengthened glasses, such as some double-ion-exchanged glasses, are characterized by refractive index profiles containing a steep region of rapidly decreasing refractive index near the surface. Such index profiles are problematic for stress measurements using the established prism-coupling technique of industry-standard FSM-6000, due to significant broadening of the coupling resonances caused by excessive coupling between the light propagating in the prism and light propagating in the waveguide region of the glass substrate formed as a result of ion exchange.

Various techniques have been invented recently to mitigate this problem. In one method a low-index layer is used to control the coupling strength. This technique allows obtaining spectra of sharp high-contrast lines, but has the inconvenience of stricter requirements for cleanliness of the contacting surface due to need for proximity (typically <1 μm) between the glass and the measurement prism. Other methods include use of higher-index oil (>1.7) to increase the index contrast and narrow the coupling resonances, and inserting a diffuser in close proximity to the prism to further flatten the angular distribution of illumination, to counteract the high sensitivity of position detection of the broadened resonances to intensity variations in the background illumination. These latter methods have helped extend the range of the convenient high-index-oil measurement (no need for sub-micron thickness of the oil layer, no need for prevention of particles from the prism-sample interface), but the precision of such measurement is often poorer compared to measurements of traditional Gorilla® glass with moderate slope $$\left|\frac{\lambda}{n}\frac{dn}{ds}\right| < 0.00016,$$

where λ is the wavelength, n is the refractive index, and z is the depth coordinate. For example, substantially steeper profiles have showed standard deviations of the surface compressive stress (CS) often substantially greater than 20, even 50 MPa, which is problematic for obtaining high-yield quality control. In comparison, standard Gorilla® glass is quite often measured with CS standard deviation below 5 MPa. Hence, further methods of improving the measurement precision for profiles containing a shallow region of steeply decreasing refractive index with depth are of great value for enabling high-yields and allowing operation closest to the desirable design conditions for the chemically strengthened glass.

SUMMARY

The residual standard deviation of the measured compressive stress after applying the methods known in the art are still elevated relative to measurements of ion exchanged alkali aluminosilicate glass such as Corning Gorilla® Glass, manufactured by Corning Incorporated, are to a large degree due to limited contrast of the coupling resonance fringes (spectral lines) of the low-order modes confined to the steep high-index region. The inadequate contrast makes the detection of the relatively broad coupling resonances susceptible to noise. In addition, the broad low-contrast spectral lines of these coupling resonances are often subject of distortion, as will be explained in the detailed description. These effects lead to increased standard deviation during measurements of the sample, as the shape of the spectral lines may depend on the thickness and wedge angle of the oils, and the detection is also sensitive to detector noise. The application of certain carefully controlled restrictions of the illumination of the coupling interface and the collection of light reflected from the coupling interface, allow substantial improvement of the contrast of the problematic coupling resonances, and substantial reduction of the distortion of the spectral lines of these resonances, leading to substantially more precise measurements of the CS. The methods described herein provide an increase in fringe contrast for strongly coupled modes, and thus more precise measurements.

In another aspect, a substantial longitudinal gradient of intensity along the light propagation direction is introduced at the prism-sample interface. The present inventors have obtained improved contrast of the coupling resonances, and reduced CS standard deviation when such gradient was introduced, compared with the case of relatively uniform intensity at the prism-sample interface. The value of the gradient is that it helps maintain a substantial positive balance between coupled and back-coupled light, substantially mitigating the formation of bright fringes of back-coupled light alongside the dark coupled-light fringes.

Accordingly, one aspect of the disclosure is to provide a method and apparatus for improving contrast in prism coupling measurements of waveguide mode spectra, wherein the measured waveguide sample has a surface and a surface region of rapidly decreasing index, characterized with normalized slope $$\left|\frac{\lambda}{n}\frac{dn}{dz}\right| > 0.0004,$$

where n=n(z) is a refractive index profile of the waveguide sample as a function of the distance z into the waveguide sample from the surface and λ is a measurement wavelength. An opaque light-blocking element is placed in the portion of the light beam closest to the plane of the contact between prism and measured sample, on the input side, output side or both sides of the prism. The light blocking element prevents light from the light source to reach a portion of the length of the prism-sample coupling interface along the optical path, prevents light reflected from a portion of the aforementioned length to reach the detector, or both when input and output light-blocking elements are used. The portion of the illuminated length from which light is allowed to reach the detector at a position corresponding to the lowest-order mode does not exceed the smaller of 7 times the maximum possible effective coupling length of the lowest-order mode, and 7 mm.

Another aspect of the disclosure is to provide a provide a method and apparatus for improving contrast in prism coupling measurements of waveguide mode spectra where the measured waveguide sample has a surface region of rapidly decreasing index, characterized with normalized slope |λ/n dn/dz|>0.0004. A light-blocking element is placed in the portion of the light beam closest to the plane of the contact between prism and measured sample on the input side, output side, or both the input and output sides of the prism. The light blocking element prevents light from the light source from reaching a portion of the length of the prism-sample coupling interface along the optical path, prevents light reflected from a portion of the aforementioned length to reach the detector, or both when input and output light-blocking elements are used. At least one of the light-blocking elements has variable transmission as a function of distance from the plane of prism-sample coupling, with transmission increasing as the distance from the aforementioned coupling plane increases. The variable-transmission light-blocking element is a non-circular aperture.

Another aspect of the disclosure is to provide a method of improving contrast in prism coupling measurements of waveguide mode spectra. The method comprises: forming a prism-sample coupling interface between a coupling surface of a prism having an input surface and an output surface and a surface of a waveguide sample; and disposing an opaque light-blocking element in a portion of a path of a light beam emanating from a light source, the portion being closest to a plane of contact between the coupling surface and the waveguide sample, wherein the opaque light blocking element is disposed in at least one of the input surface and the output surface. The waveguide sample has a surface region of decreasing index with normalized slope $$\frac{\lambda}{n}\frac{dn}{ds} > 0.0004$$

extending from the surface into the waveguide sample and the prism, where n=n(z) is a refractive index profile or the waveguide sample as a function of the distance z into the waveguide sample from the waveguide sample surface and λ is a wavelength of the light beam. The opaque light blocking element prevents at least a portion of the light beam from reaching a portion of the prism sample coupling interface along the path of the light beam, prevents a first portion of light reflected from the prism-sample coupling interface to reach a detector, and allows a second portion of light reflected from the prism-sample coupling interface to reach the detector. The second portion reaches the detector at a position corresponding to a lowest-order mode, and does not exceed the smaller of 7 times the maximum possible effective coupling length of the lowest-order mode, and 7 mm.

In another aspect, a method of improving contrast in prism coupling measurements of waveguide mode spectra is provided. The method comprises: forming a prism-sample coupling interface between a coupling surface of a prism with a surface of a waveguide sample, the waveguide sample having a surface region of decreasing index with normalized slope |λ/n dn/dz|>0.0004 extending from the surface into the waveguide sample and the prism having an input surface and an output surface and the prism having an input surface and an output surface; and disposing an opaque light-blocking element on at least one of the input surface and the output surface and in a portion of a path of a light beam emanating from a light source, the portion being closest to a plane of contact between the coupling surface and the waveguide sample. The opaque light blocking element prevents a first portion of light reflected from the prism-sample coupling interface to reach a detector and allows a second portion of light reflected from the prism-sample coupling interface to reach the detector at a position corresponding to a lowest-order mode, and does not exceed the smaller of 7 times the maximum possible effective coupling length of the lowest-order mode, and 7 mm.

These and other aspects, advantages, and salient features will become apparent from the following detailed description, the accompanying drawings, and the appended claims.

DETAILED DESCRIPTION

Figure 1:
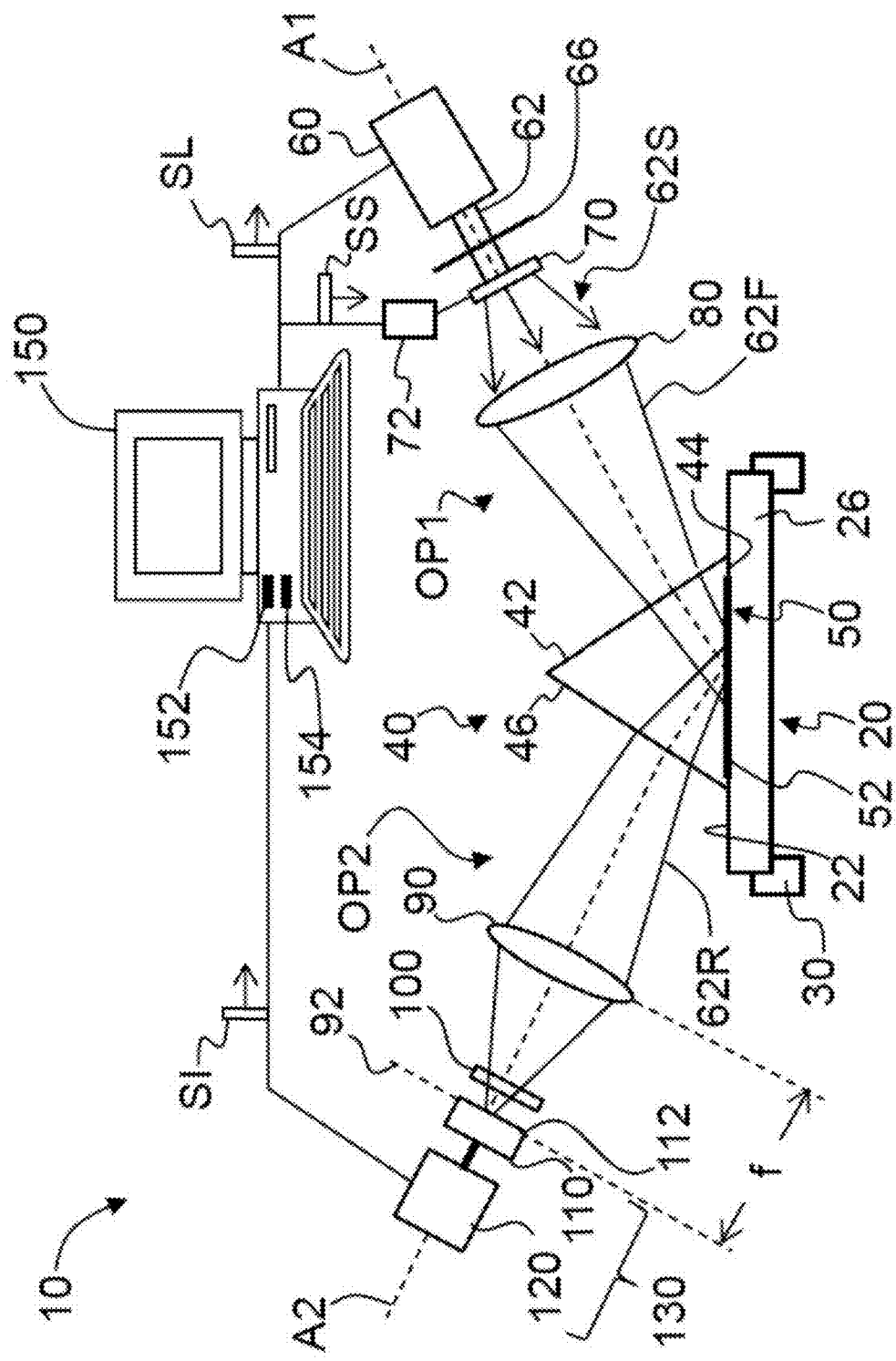
FIG. 1 is a schematic diagram of an example prism-coupling system.

In the following description, like reference characters designate like or corresponding parts throughout the several views shown in the figures. It is also understood that, unless otherwise specified, terms such as "top," "bottom," "outward," "inward," and the like are words of convenience and are not to be construed as limiting terms. In addition, whenever a group is described as comprising at least one of a group of elements and combinations thereof, it is understood that the group may comprise, consist essentially of, or consist of any number of those elements recited, either individually or in combination with each other. Similarly, whenever a group is described as consisting of at least one of a group of elements or combinations thereof, it is understood that the group may consist of any number of those elements recited, either individually or in combination with each other. Unless otherwise specified, a range of values, when recited, includes both the upper and lower limits of the range as well as any ranges therebetween. As used herein, the indefinite articles "a," "an," and the corresponding definite article "the" mean "at least one" or "one or more," unless otherwise specified. It also is understood that the various features disclosed in the specification and the drawings can be used in any and all combinations.

As used herein, the terms "glass article" and "glass articles" are used in their broadest sense to include any object made wholly or partly of glass. Unless otherwise specified, all compositions are expressed in terms of mole percent (mol %).

Compressive stress and depth of layer are measured using those means known in the art. Such means include, but are not limited to, measurement of surface stress (FSM) using commercially available instruments such as the FSM-6000, manufactured by Luceo Co., Ltd. (Tokyo, Japan), or the like, and methods of measuring compressive stress and depth of layer are described in ASTM 1422C-99, entitled "Standard Specification for Chemically Strengthened Flat Glass," and ASTM 1279.19779 "Standard Test Method for Non-Destructive Photoelastic Measurement of Edge and Surface Stresses in Annealed, Heat-Strengthened, and Fully-Tempered Flat Glass," the contents of which are incorporated herein by reference in their entirety. Surface stress measurements rely upon the accurate measurement of the stress optical coefficient (SOC), which is related to the birefringence of the glass. SOC in turn is measured by those methods that are known in the art, such as fiber and four point bend methods, both of which are described in ASTM standard C770-98 (2008), entitled "Standard Test Method for Measurement of Glass Stress-Optical Coefficient," the contents of which are incorporated herein by reference in their entirety, and a bulk cylinder method.

Referring to the drawings in general and to FIG. 1 in particular, it will be understood that the illustrations are for the purpose of describing particular embodiments and are not intended to limit the disclosure or appended claims thereto. The drawings are not necessarily to scale, and certain features and certain views of the drawings may be shown exaggerated in scale or in schematic in the interest of clarity and conciseness.

FIG. 1 is a schematic diagram of an example prism-coupling system ("system") 10 suitable for carrying out the methods of measuring the TE and TM mode spectra for ion-exchanged substrate 20 as disclosed herein, containing the steep and shallow near-surface region R1. In an example, ion-exchanged substrate 20 constitutes a chemically strengthened glass such as GORILLA® glass, made by Corning, Incorporated, of Corning, N.Y.

The system 10 includes a substrate holder 30 configured to hold substrate 20. In alternative embodiments, however, substrate holder 30 is not required. System 10 also includes coupling prism 40 that includes an input surface 42, a coupling surface 44, and an output surface 46. The coupling prism 40 has a refractive index $n_p > n_s$. The coupling prism 40 is interfaced with substrate 20 by bringing coupling-prism coupling surface 44 and substrate top surface 22 into optical contact, thereby defining a substrate-prism interface ("interface") 50 that includes an interfacing fluid 52. Details of how coupling prism 40 is interfaced with ion-exchanged substrate 20 are discussed below.

In an example embodiment, coupling prism 40 has a trapezoidal, curved, or other cross-sectional shape instead of the triangular cross-sectional shape that is shown in FIG. 1 by way of illustration. The term "curved" here refers to cases where the input surface 42 and/or output surface 46 may be curved, such as cylindrical or spherical surfaces.

With continuing reference to FIG. 1, system 10 includes optical axes A1 and A2 that respectively pass through input and output surfaces 42 and 46 of coupling prism 40 to generally converge at interface 50 after accounting for refraction at the prism/air interfaces. The system 10 includes, in order along axis A1, a light source 60 that emits measuring light 62 of wavelength λ, an optional optical filter 66 that may be alternatively included in the detector path on axis A2, an optional light-scattering element 70 that forms scattered light 62S, and an optional focusing optical system 80 that forms focused (measuring) light 62F, as explained below. Thus, in an example of system 10, there are no optical elements between light source 60 and prism input surface 42.

The system 10 also includes, in order along axis A2 from coupling prism 40, a collection optical system 90 having a focal plane 92 and a focal length f and that receives reflected light 62R as explained below, a TM/TE polarizer 100, and a photo detector system 130. The axis A1 defines the center of an optical path OP1 between light source 60 and coupling-prism coupling surface 44. The axis A2 defines the center of an optical path OP2 between coupling surface 44 and photo detector system 130. Note that axes A1 and A2 may be bent at input and output surfaces 42 and 46, respectively, due to refraction. They may also be broken into sub-paths by insertion of mirrors in optical paths OP1 and/or OP2.

Figure 2:
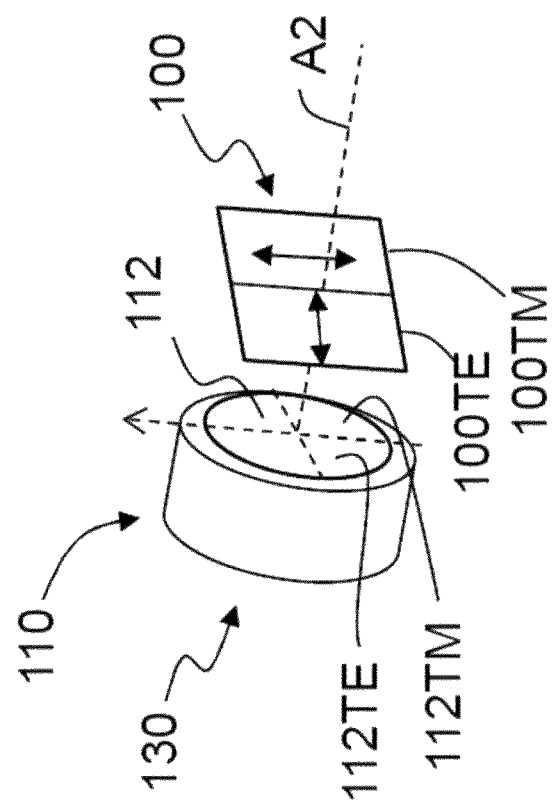
FIG. 2 is a schematic close-up view of the photo detector system of the prism-coupling system of FIG. 1.

In an example, photo detector system 130 includes a detector (camera) 110 and a frame grabber 120. In other embodiments discussed below, photo detector system 130 includes a CMOS or CCD camera. FIG. 2 is a close-up elevated view of the TM/TE polarizer and detector 110 of photo detector system 130. The photo detector system 130 includes a photosensitive surface 112. The photosensitive surface 112 resides in focal plane 92 of collecting optical system 90, with the photosensitive surface being generally perpendicular to axis A2. This serves to convert the angular distribution of reflected light 62R exiting the coupling prism output surface 46 to a transverse spatial distribution of light at the sensor plane of camera 110. In an example embodiment, photosensitive surface 112 comprises pixels; i.e., detector 110 is a digital detector, e.g., a digital camera.

Splitting photosensitive surface 112 into TE and TM sections 112TE and 112TM allows for the simultaneous recording of digital images of the angular reflection spectra (mode spectra) for the TE and TM polarizations of reflected light 62R. This simultaneous detection eliminates a source of measurement noise that could arise from making the TE and TM measurements at different times, given that system parameters can drift with time.

Example light sources 60 include lasers, light-emitting diodes, and broader-bandwidth sources such as hot-filament lamps and quartz lamps. Example operating wavelengths λ of light 62 generated by light source 60 can include near-ultra-violet, visible and infrared wavelengths.

The system 10 includes a controller 150, which is configured to control the operation of the system. The controller 150 is also configured to receive and process image signals SI from photo detector system 130 that are representative of captured TE and TM mode spectra images. The controller 150 includes a processor 152 and a memory unit ("memory") 154. The controller 150 may control the activation and operation of light source 60 via a light-source control signal SL, and receives and processes image signals SI from photo detector system 130 (e.g., from frame grabber 120, as shown).

In an example, controller 150 comprises a computer and includes a reading device, for example, a floppy disk drive, a CD-ROM drive, a DVD drive, a magnetic optical disk (MOD) device (not shown), or any other digital device including a network-connecting device, such as an Ethernet device (not shown), for reading instructions and/or data from a computer-readable medium, such as a floppy disk, a CD-ROM, a DVD, a MOD, a flash drive, or another digital source such as a network or the Internet. The controller 150 is configured to execute instructions stored in firmware and/or software (not shown), including signal-processing instructions for carrying out the surface birefringence/stress measurements disclosed herein. In examples, the terms "controller" and "computer" are interchangeable.

The controller 150 is programmable to perform the functions described herein, including the operation of system 10 and the aforementioned signal processing of image signals SI in order to arrive at a measurement of the stress characteristics of substrate 20, such as the stress profile S(x), birefringence, or compressive stress CS. As used herein, the term "computer" is not limited to just those integrated circuits referred to in the art as computers, but broadly refers to computers, processors, microcontrollers, microcomputers, programmable logic controllers, application-specific integrated circuits, and other programmable circuits, and these terms are used interchangeably herein.

Software may implement or aid in the performance of the operations of system 10 disclosed herein, including the aforementioned signal processing. The software may be operably installed in controller 150 and in particular in processor 152 and memory 154. Software functionalities may involve programming, including executable code, and such functionalities may be used to implement the methods disclosed herein. Such software code is executable by the general-purpose computer or by the processor unit described below.

In operation, the code and possibly the associated data records are stored within a general-purpose computer platform, within processor 152 and/or in memory 154. At other times, however, the software may be stored at other locations and/or transported for loading into the appropriate general-purpose computer systems. Hence, the embodiments discussed herein involve one or more software products in the form of one or more modules of code carried by at least one machine-readable medium. Execution of such code by processor 152 of computer system 150 or by the processor unit enables the platform to implement the catalog and/or software downloading functions in essentially the manner performed in the embodiments discussed and illustrated herein.

The controller 150 and/or processor 152 may each employ a computer-readable medium or machine-readable medium (e.g., memory 154), which refers to any medium that participates in providing instructions to the processor for execution, including, for example, determining an amount of surface birefringence/stress or the stress profile S(x) of substrate 20. The memory 154 constitutes a computer-readable medium. Such a medium may take many forms, including but not limited to non-volatile media, volatile media, and transmission media. Non-volatile media include, for example, optical or magnetic disks, such as any of the storage devices in any computer(s) operating as one of the server platforms discussed above. Volatile media include dynamic memory, such as the main memory of such a computer platform. Physical transmission media include coaxial cables, copper wire, and fiber optics, including the wires that comprise a bus within a computer system.

Common forms of computer-readable media therefore include, for example, a floppy disk, a flexible disk, a hard disk, magnetic tape, flash drives and any other magnetic medium; a CD-ROM, a DVD and any other optical medium; less commonly used media such as punch cards, paper tape and any other physical medium with patterns of holes; a RAM, a PROM, an EPROM, a FLASH-EPROM and any other memory chip or cartridge; a carrier wave transporting data or instructions, cables or links transporting such a carrier wave, or any other medium from which a computer can read programming code and/or data. Many of these forms of computer-readable media may be involved in carrying one or more sequences of one or more instructions to processor 152 for execution.

In an example, controller 150 is programmed to determine at least one characteristic of ion-exchanged substrate 10 based on the measured mode spectra. Example characteristics include: surface stress, stress profile, compressive stress, depth of layer, refractive index profile, and birefringence. In an example, controller 150 is programmed to carry out calculations as disclosed in the article by A. Brandenburg, "Stress in Ion-Exchanged Glass Waveguides," Journal of Lightwave Technology, Vol. LT-4, No. 10, October 1986, pp. 1580-93.

System 10 may be a modified version of a commercial prism-coupling instrument, such as the FSM-6000 prism-coupling instrument made and sold by Orihara Industrial Co., Ltd., of Tokyo, Japan. The FSM-6000 instrument represents the state of the art in high-throughput non-destructive measurements of stress in flat ion exchanged glasses, and utilizes a coupling prism 40 with a prism index $n_p$=1.72 at 589 nm. The FSM-6000 uses an index-matching fluid having an index $n_f$=1.64. In the FSM-6000 instrument, the surface compressive stress (CS) is calculated from the effective indices $n_{eff}$ of the first two transverse magnetic (TM) and the first two transverse electric (TE) modes, while the total number of observed modes is used along with the substrate index and the aforementioned effective indices of the first 2 modes for the depth of layer (DOL) calculation based on a linear refractive-index profile assumption.

Figure 3:
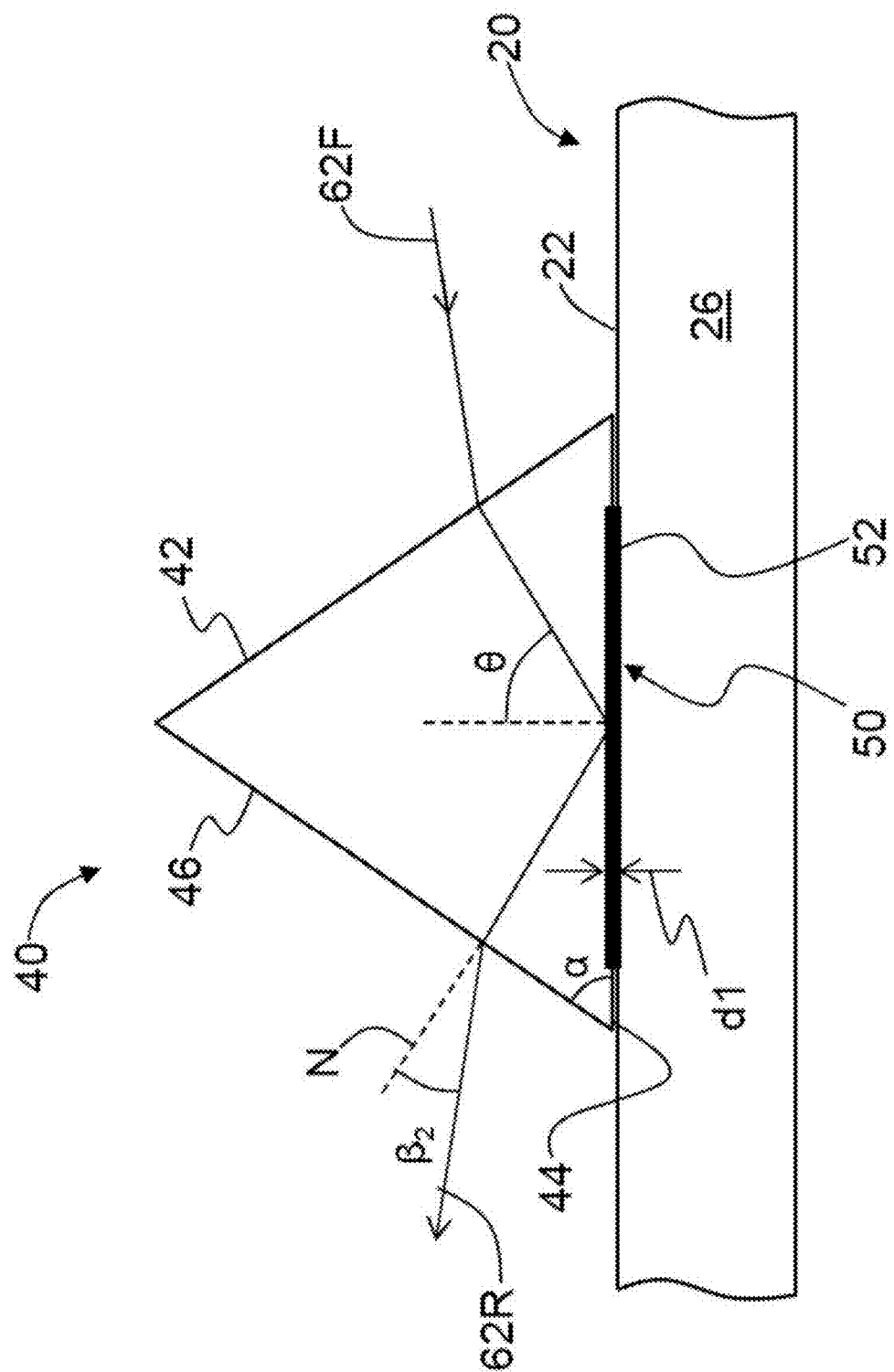
FIG. 3 is a schematic close-up view of an example coupling prism interfaced with the ion-exchanged substrate using an interfacing fluid having a thickness d1 and a refractive index $n_f$.

FIG. 3 is a close-up cross-sectional view of coupling prism 40 as interfaced with ion-exchanged substrate 20 using interfacing fluid 52. The coupling prism angle α is shown, along with the coupling angle θ, exit angle $β_2$ and surface normal N. Interfacing fluid 52 has a thickness d1 and the aforementioned fluid index $n_f$. An example type of interfacing fluid is oil, such as index-matching oil.

The use of interfacing fluid 52 is not as an index matching layer per se, but as a "potential barrier" whose parameters can be used to control the strength of coupling of measuring light 62F between coupling prism 40 and substrate 20. In this manner, despite the large number of bounces per unit propagation length, the intensity of measuring light 62F coupled to a near-surface mode can be made to decay slower with propagation distance. This can allow for narrower and deeper (and thus sharper) coupling resonances than when an index-matching fluid is used. For that purpose, instead of selecting oil with an index higher than that of the measured modes, the interfacing fluid 53 having a refractive index that is lower than that of the measured modes, i.e., $n_f < n_{eff}$, is selected.

In an example embodiment, the thickness d1 of interfacing fluid 52 is at least as large as a threshold thickness $d1_{TH}$ that prevents over-coupling, limiting the error that would be caused by the high sensitivity of mode birefringence $B_m$ to the thickness d1.

System 10, photo detector system 110, and coupling prism are described in U.S. Provisional Patent Application No. 61/897,546, filed Oct. 30, 2013, by Rostislav Vatchev Roussev et al., and entitled "Apparatus and Methods for Measuring Mode Spectra for Ion-Exchanged Glasses Having Steep Index Region;" and U.S. Provisional Patent Application No. 61/860,560, filed Jul. 31, 2013, by Rostislav Vatchev Roussev et al., and entitled "Prism Coupling Methods with Improved Mode Spectrum Contrast for Double Ion-Exchanged Glass." the contents of these applications are incorporated herein by reference in their entirety.

Figure 4:
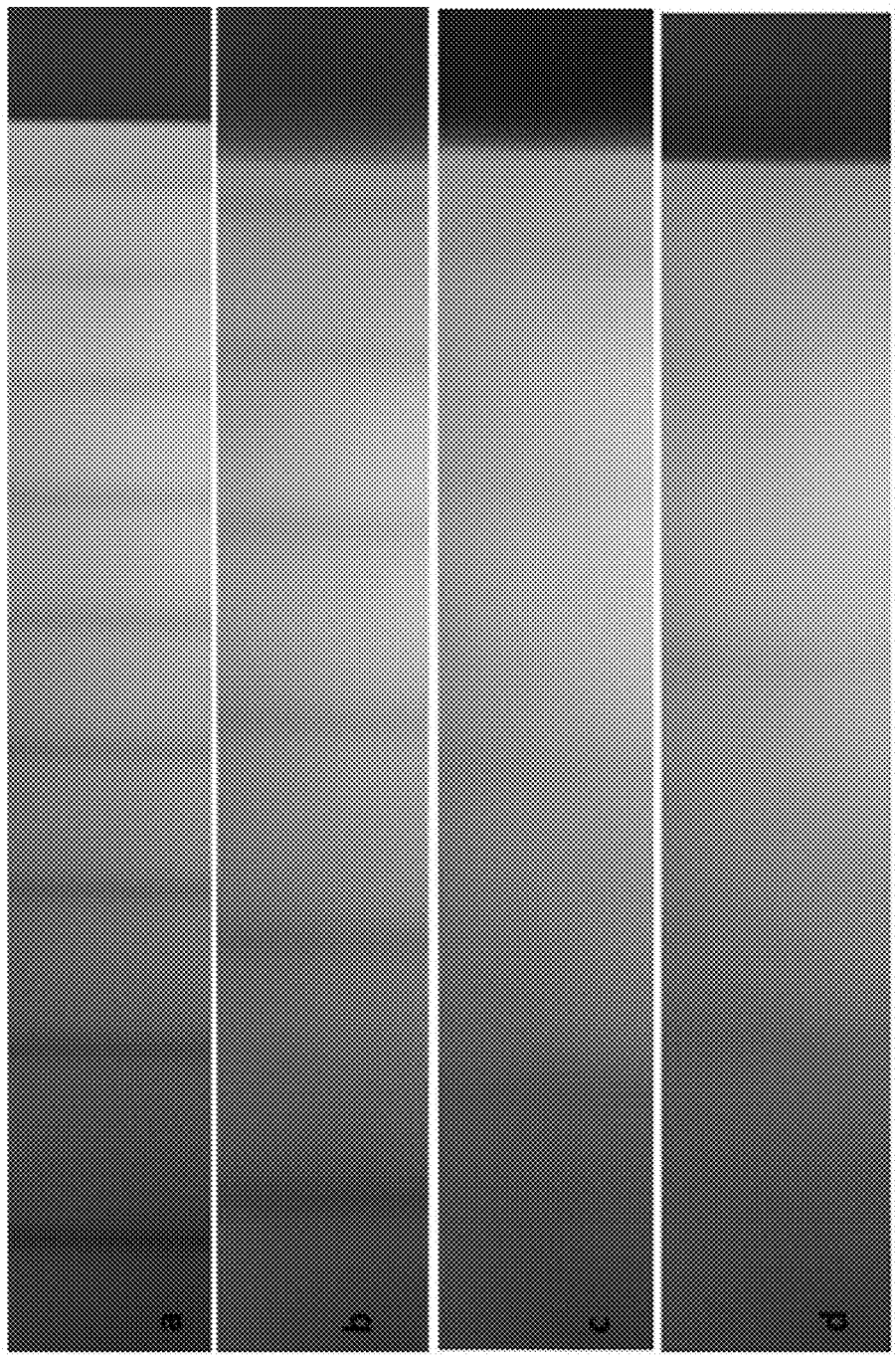
FIG. 4 shows mode coupling spectra of ion exchanged regions with Δn≈0.015 and depths of layer (DOLs) of 21, 14, 10, and 8.2 μm for photographs a, b, c, and d, respectively.

FIG. 4 shows mode coupling spectra of ion exchanged regions with $\Delta n \approx 0.15$ and DOLs of 21, 14, 10, and 8.2 µm, respectively, for photographs a, b, c, and d. The normalized slope of the index profile $$\frac{\lambda}{n}\frac{dn}{dz}$$

is approximately −0.0003, −0.0004, −0.0006, and −0.0007 for spectra a, b, c, and d, respectively, where n=n(z) is the refractive index profile of the substrate 20 as a function of the distance z into the substrate from substrate surface 22, and λ is a wavelength of measuring light 62. FIG. 4 illustrates how the contrast of the coupling resonances (dark fringes in the figure) is significantly deteriorated, and the widths are significantly increased for $$\left|\frac{\lambda}{n}\frac{dn}{dz}\right| > 0.0004.$$

This effect causes difficulties for automatic capture of the modes of shallow steep regions in the presence of image noise. In addition, when the modes are successfully captured, the measured stress is subject to significant standard deviations, which is problematic due to need for precise process and quality control.

Coupling spectra have poor contrast when the mode coupling is strong. The present inventors have realized that the poor contrast for the low-order, strongly-coupled modes of waveguides having a shallow region of steep variation of refractive index, leads to a large standard deviation when measuring stress in the presence of noise. This is particularly true for doubly-ion-exchanged parts, where chemical strengthening is first obtained through K for Na ion exchanged, and anti-microbial efficacy is enabled through a second ion exchange that introduces in a near-surface region of the glass. The same problem is also observed when a short ion exchange in a K-rich salt produces a shallow region where the $K_2O$ concentration decreases by >5 mol-% from the surface to a depth of about 5 µm (FIG. 4 c,d). The problem similarly occurs in measurements of double-ion-exchanged profiles where the a first long ion exchange in a bath containing both $NaNO_3$ and $KNO_3$ with NaNO3 concentration >20 weight-% produces a deep profile with relatively small slope, and a second short ion exchange in a bath with low $NaNO_3$ content (<2 weight-%) produces a shallow region near the surface where the $K_2O$ concentration decreases by more than about 5 mol-% in the first 5 microns.

In one example, this disclosure pertains to measurements using a prism-coupling system such as FSM-6000, which is used for measuring stress. In this system, the prism has a refractive index of 1.72, the measured glass substrate has an index of about 1.5, and a liquid (oil) with refractive index intermediate between that of the prism and the sample surface is used to allow the light to pass between prism and substrate, thus allowing coupling. In another example, the liquid between the prism and the substrate may have index lower than that of the substrate, but the coupling of the low-order modes that are confined to the shallow steep region is still significantly stronger than that for the high-order modes spread over the deep region of the waveguide, leading to reduced precision of measurement of the low-order modes.

The poor contrast for the low-order modes is due to two main factors. First, the stronger coupling for the low-order modes leads to broadening of the coupling resonances, through a relationship between coupling strength and resonance width. The broadening may be reduced by reducing the coupling strength; e.g., by increasing the index difference between the index oil used to enable coupling between the prism and the sample. For example, increasing the oil index from the commonly used value of 1.64 to the value of 1.72, equal to the prism index helps narrow the resonances and improve contrast. The strength of coupling may also be controlled by using a low-index region between the substrate and the prism. This method allows more substantial reduction of the width of the coupling resonances, but even in this case the low-order modes may be broad in some cases, when their coupling has to be increased in order to achieve adequate coupling for the higher-order modes of the deep region of the profile. Hence, additional methods to further increase contrast are of value even in this case.

The second mechanism that has been found to reduce contrast is the balance between light coupling into the guided modes of the ion-exchanged region, and light coupling from these guided modes back to the prism. In particular, when dark-line measurements are performed on the angular spectrum of reflection from the prism-sample interface, the measurement relies on light coupling into the guided modes to be absent in the reflection spectrum, thus resulting in a dark line at the corresponding coupling angles. If light couples back from a particular guided mode to the prism, then it ends up increasing intensity at the location of the dark line on the detector that corresponds to the angle of coupling of that mode, resulting in reduced contrast for the resonance of that mode.

Figure 5:
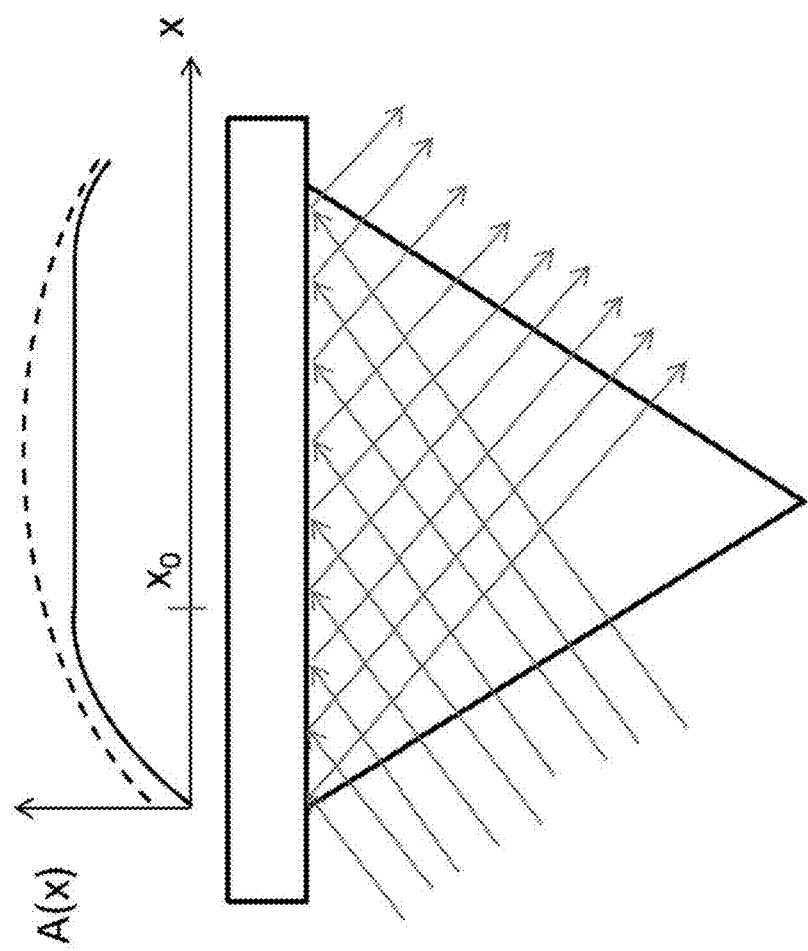
FIG. 5 is an illustration of two distributions of electric field amplitude of light coupled in the waveguide of the substrate from a particular plane wave along the coupling interface between coupling prism and measured substrate.

FIG. 5 is an illustration of two typical distributions of electric field amplitude of light coupled in the waveguide of the substrate from a particular plane wave along the coupling interface between coupling prism and measured substrate. The distance $x_0$ illustrates the distance over which the amplitude substantially increases along the propagation direction x. When the illumination of the prism coupling facet is relatively uniform, the distance $x_0$ is approximately equal to maximum coupling length for the mode that is strongly coupled to the prism. The portions of the waveguide where the field distribution is flat or decreasing along x, contribute a decrease in contrast of the dark spectral lines.

Let x be the direction along the prism-substrate interface that goes from the side of the light source to the side of the detector (FIG. 5). Looking at a particular angle of illumination from the prism side, if the amplitude of the electric field at the prism contact surface contributed by the illuminating wave at that angle is uniform along the prism-substrate interface, then the amplitude A(x) of light coupled into the waveguide increases along x as more light couples into the waveguide. As the amount of light in the waveguide increases with x, light starts coupling back to the prism, and the rate of increase of the light amplitude in the waveguide becomes smaller. If coupling is strong, a condition can occur where a saturation of the amplitude of light in the waveguide mode is obtained at a location x0 somewhere between the input and output end of the waveguide-prism interface. For the portion of the waveguide with x>x0 where the mode field amplitude along the waveguide is constant, the net coupling from the prism to the waveguide is approximately 0, since for in that portion similar amount of light couples back from the waveguide to the prism as the amount of light coupling from the prism to the waveguide. In the image of the spectrum at the detector, light reflected from locations with x>x0 does not contribute useful signal, but it does increase the illumination background, therefore leading to decrease in contrast. A portion of the waveguide near the prism exit facet has decreasing mode field amplitude with increasing x. This portion has an even worse effect on the contrast, as in it more light couples from the waveguide to the prism than vice versa, contributing a brightness increase at the particular exit angle corresponding to the dark line of the mode in question, severely decreasing the contrast of that mode's line measured relative to the background at neighboring angles.

Figure 6:
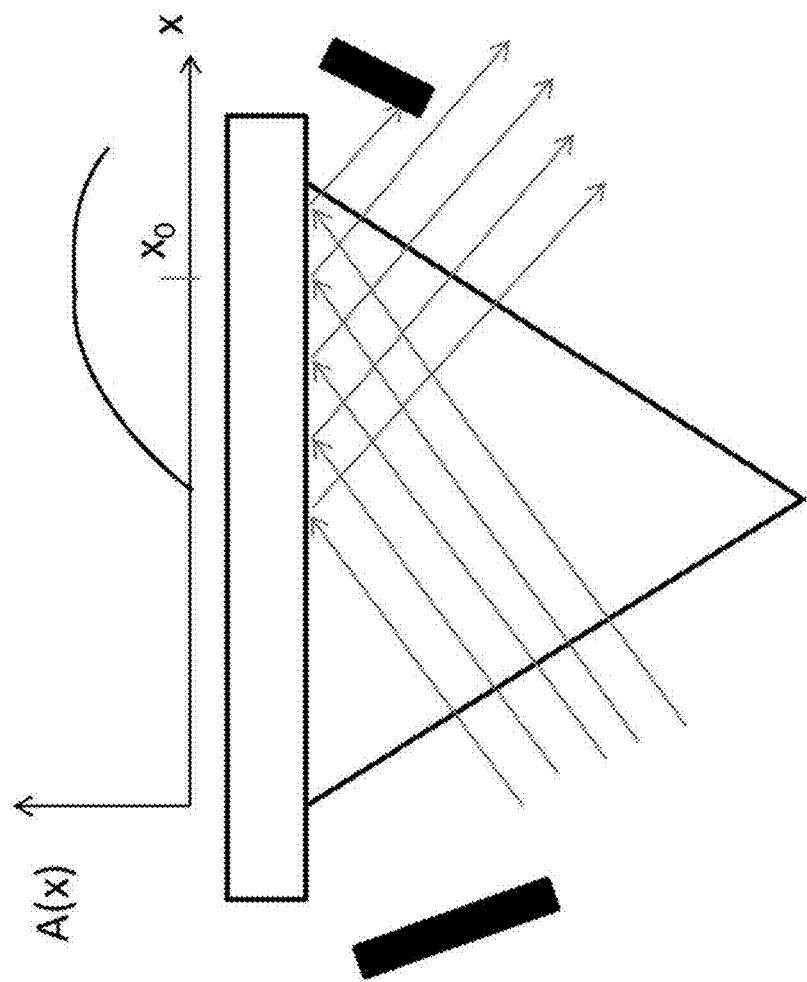
FIG. 6 is an illustration showing a light block inserted in the top portion of the input beam to reduce the length of the portion having relatively uniform waveguide mode field amplitude along x, while retaining the portion having fast growing amplitude along x of the field in the waveguide due to coupling of light from the prism.

To counteract these effects, the present disclosure provides three types of solutions. In one embodiment, a light block or aperture is inserted that shifts the beginning of illumination closer to the end of the prism, thus reducing the fraction of the constant-amplitude region with x>x0, and thus its negative effect on contrast. FIG. 6 shows a light block inserted in the top portion of the input beam can be used to reduce the length of the portion having relatively uniform waveguide mode field amplitude along x, while retaining the portion having fast growing amplitude along x of the field in the waveguide due to coupling of light from the prism. A second light block inserted in the top portion of the exit beam blocks light out-coupled from the portion of the waveguide that has amplitude that is flat or decreasing along x. Both light blocks work to mitigate the loss of contrast due to portions of flat or decreasing field amplitude (or intensity) in the waveguide mode along x. An example distribution of the electric field amplitude A(x) along the guide for that case is also included in FIG. 6, showing a substantial reduction of the constant-amplitude region. This solution may have in some cases a negative side-effect of broadening some of the narrower spectral lines of the higher-order modes, because it leads to a decrease of the effective beam aperture by the ratio of the blocked portion of the light beam along x to the total length of prism-sample interface. In some cases another negative side effect may occur, as the part of the angular spectrum associated with the low-order guided modes experiences a much more significant decrease in intensity compared to the part corresponding to the high-order modes. This may lead to a substantial and varying slope of the intensity background as a function of angle, against which the dark lines corresponding to the guided modes are detected. In turn, it may introduce some error in the measurements due to slight shifting of the positions of the intensity minima corresponding to the modes. This effect can be mitigated by adjusting the height of the distant light source and taking advantage of an angular gradient of the light source of the opposite sense.

In another embodiment, the solution involves inserting a light block in the exit beam (also illustrated in FIG. 6), that blocks light coming from the region of decreasing mode field amplitude along x, and optionally from the region of near-constant mode field amplitude along x. In fact, a combination of a light block inserted in the input beam and another light block inserted in the output beam allows the maximum flexibility for mitigating the effects of decreased mode contrast for strongly coupled modes.

In one example, substantial improvement in contrast and decrease of standard deviations of measurement of surface compressive stress (CS) from >50 MPa to <10 MPa for anti-microbial Gorilla® glass has been observed by insertion of light blocks on the input and output and output side of the light beam. The light blocks were vertical, placed symmetrically a distance of approximately 12 mm from the middle of the prism on either side, and with the lower end of the light blocks positioned 5 mm below the plane of the prism-sample coupling interface. The portions of the input and output beam above the 5 mm depth of the light block were completely blocked. In another example, the standard deviation of CS was reduced to a range of 5-15 MPa for Gorilla® glass samples having a region of steep decline of K concentration in the top 10 microns by placing light blocks at the same locations symmetrically on either side of the prism, such that the bottom of the light blocks was 4 mm below the plane of the prism-sample coupling interface. The portions of the input and output light beam above the bottom of the light blocks were completely blocked. In both examples, the light blocks were implemented as opaque rectangles of black sticky tape with thickness between 100 μm and 200 μm.

Figure 7:
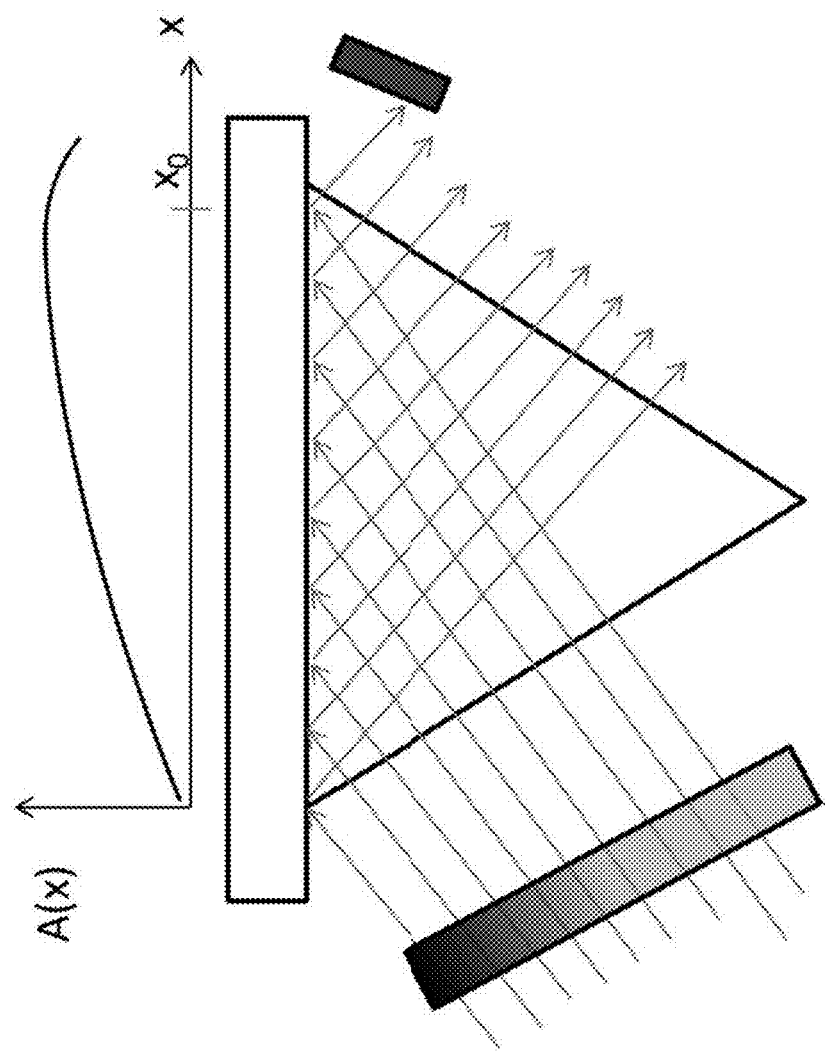
FIG. 7 is an illustration showing a variable attenuator inserted in the input beam.

In yet another embodiment, the solution involves introducing a gradient of the illumination of the prism base along the x axis, as shown in FIG. 7, which is an illustration showing a variable attenuator inserted in the input beam. With increasing attenuation toward the top of the beam, the attenuator can be used to stretch the portion of increasing amplitude of the waveguide mode along x, at the expense of portions of constant or decreasing amplitude along x, helping to mitigate the effect of contrast decrease due to portions of the constant, or decreasing amplitude along x. In particular, for better detection of dark lines, a positive gradient of the illumination is proposed, where the field intensity of the prism base increases along x. In this case, the region of increasing amplitude of the field inside the waveguide is stretched along the x axis toward the prism exit facet on the detector side. This continuous increase of amplitude A(x) along the x axis helps reduce the effect of increasing background that a constant-amplitude region would normally contribute. In the example shown in FIG. 7, this is achieved by inserting an attenuator that has a gradient of attenuation on the source side, starting with high attenuation on the side closer to the prism-sample interface, and reduced attenuation on the bottom side closer to the prism edge opposing the coupling interface.

A similar effect can be achieved by inserting the gradient attenuator on the detector side. In this case, the distribution of field amplitude in the waveguide will be similar to that of FIG. 5 with an extended region of near-constant amplitude. However, the gradient attenuator can be arranged with its high-attenuation side closer to the coupling interface, providing strong attenuation for light coming from the constant-amplitude and decreasing-amplitude regions, thus reducing the signal-poor background. At the same time, it will provide weak attenuation for light coming from the region x<x0, which has high contrast.

Any combination of the three embodiments described hereinabove produces another embodiment that can be used to enhance contrast. For example, a spatially variable attenuator can have a portion at the top (dark side) that completely blocks light, making it a combined variable attenuator/light block, which can be placed on the input side, output side, or both.

Figure 8B:
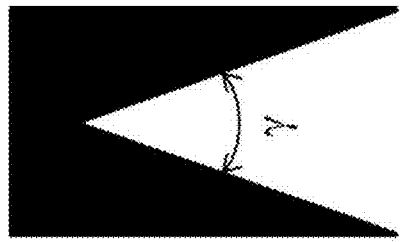
FIGS. 8A and 8B is an illustration showing two examples of spatially variable attenuators that can be used in the configuration shown in FIG. 7.
Figure 8A:
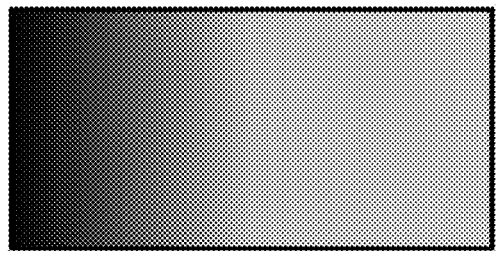

FIGS. 8A and 8B show two implementations of spatially variable attenuators that can be used in the configuration of FIG. 7. FIG. 8A shows the aforementioned gradient attenuator, with attenuation coefficient increasing from bottom to top. The gradient attenuator is a partially transparent substrate or film with insignificant scattering and absorption varying from low scattering/absorption near the bottom to high scattering/absorption near the top, causing transmission to decrease very significantly near the top. FIG. 8B shows a light block with a shape that passes more light near the bottom and less light near the top, through varying width of the central opening with vertical coordinate along the height direction. FIG. 8B achieves a similar effect averaged over the width of the prism/light beam, by having a smaller portion of the block open near the top. The angle γ can be used to control the gradient of distribution of illumination along the prism-substrate interface, and as a result, the gradient of the distribution of mode field amplitude along the waveguide.

The angle γ controls the rate of change of intensity along x. The improvement of contrast and standard deviation of measurement of surface compression for doubly-ion-exchanged samples, where the first ion exchange was produced in molten $KNO_3$ bath, while the second was produced in a $KNO_3$ bath containing up to 0.6 weight-% $AgNO_3$ has been determined. Substantial improvement in contrast was obtained when the top 2-3 mm of the input beam were blocked entirely at a position 12 mm before the prism center, and the angle was about 30, 40, and 50 degrees. Of these, the best performance was observed when the angle was about 40 degrees. The optimum rate of change of illumination intensity along x may depend on the strength of coupling of the lowest-order modes that are usually most challenging to measure automatically.

The distance $x_0$ can be called the effective useful interaction length $L_{eff}$, which in the case of uniform illumination is equal to $\iota_m$, where $\iota_m$ is the length over which the optical field of mode m decreases by a factor of e along the waveguide due to coupling or other losses, in a region where no external light is being coupled into the waveguide. In the example shown in FIG. 4, the prism length was 25 mm, while useful interaction length of the modes in examples c and d in FIG. 4 was less than 3 mm, leading to poor contrast. In the examples of anti-microbial glass, the low-order modes had useful interaction length below 1.6 mm, in some cases below 1 mm, and the prism length was 12 mm. The insertion of light blocks reduced the length from which signal was collected to about 7 mm. In general, a substantial improvement in contrast is observed when the length from which signal is collected by the camera is reduced below $7L_{eff}$, the light from the region of increasing mode amplitude along x is collected, and the light from the region of the decreasing mode amplitude along x is substantially rejected by a light block on the detector side. Preferably, the light blocks ensure that the signal is collected from an illuminated portion of the prism-sample interface that is reduced below $5L_{eff}$ by the combination of light blocks.

Prior-art systems typically contain an aperture in the detector side, but it generally accepts signal from a length greater than 10 mm. In addition, prior-art systems have the prism coupling facet raised about 0.5 mm above an instrument top surface. Portions of the system may block a small portion from the top of the light beam, which may vary slightly depending on the part of the angular spectrum in which the system is used. In general, prior-art systems are designed such that light is collected from most of the prism length, which may be 12 mm or 25 mm in actual prior-art examples. In the apparatus and method described herein, the light blocks ensure that signal in the camera is collected from illuminated length that does not exceed 8 mm, and better results are obtained when the illuminated length is reduced below about 5 mm.

Figures 9A, 9B:
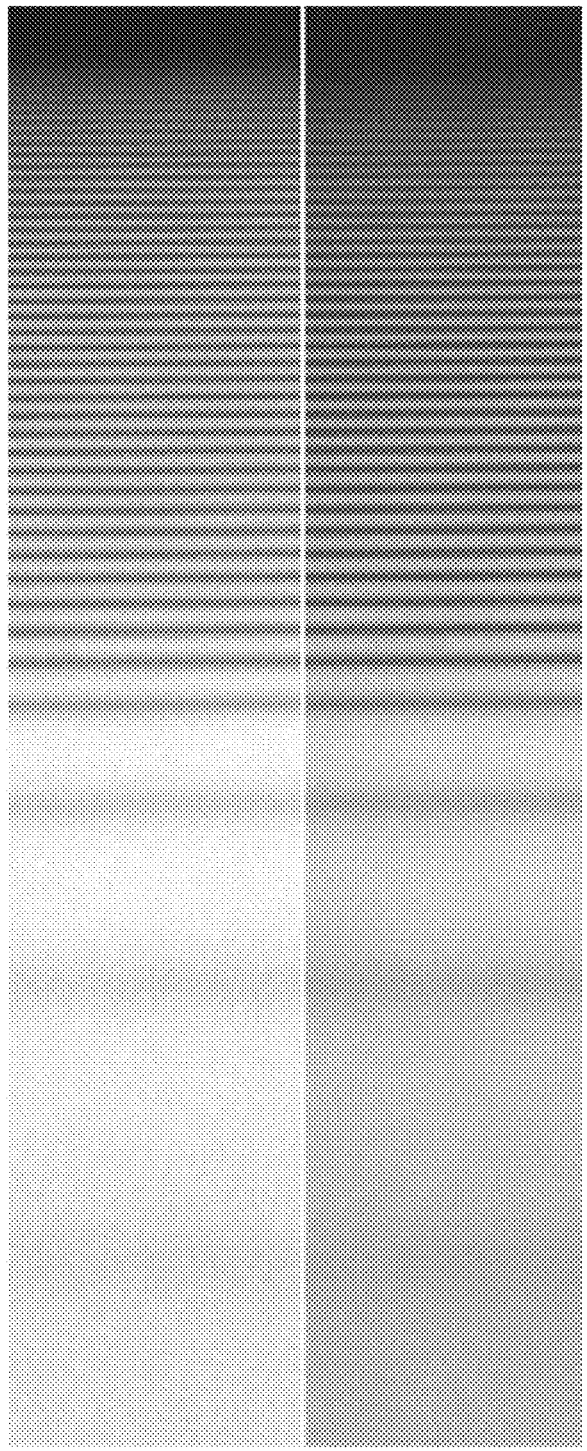
FIG. 9A is a TM-mode spectrum of a double-ion-exchanged waveguide measured without light blocking.
FIG. 9B is a TM-mode spectrum of a double-ion-exchanged waveguide measured with a light block placed on the input side of the prism from the prism center, and a light block placed on the output side of the prism.

FIG. 9A shows the TM-mode spectrum of a double-ion-exchanged waveguide measured without light blocking, whereas the lower image shows the TM-mode spectrum of a double-ion-exchanged waveguide measured with a 4.5 mm light block placed on the input side of the prism 12 mm from the prism center, and a 3 mm light block placed on the output side of the prism, also 12 mm from the center. The slight improvement in contrast for the low-order modes (left-most fringes in FIGS. 9A and 9B) confined to the shallow steep region of the profile allowed substantial decrease in standard deviation of the surface-stress measurement. At the same time, the light blocking caused the two rightmost fringes of the spectra to be lost as evidenced by the shift in the position of the transition from bright fringe pattern to dark area without detectable fringes from the top image to the bottom image.

FIGS. 9A and 9B illustrate a problem when light blocking is used to improve the contrast of low-order modes of a profile that has both a shallow steep region and a very deep region of slow decrease of refractive index. When the light block is placed relatively close to the prism (in this example it is 12 mm from the prism center, and 6 mm from the closest prism edge), it reduces the effective interaction length for all modes by approximately the same amount, leading to broadening of the normally very narrow fringes of the high-order modes propagating mainly in the very deep region of the profile. This broadening can lead to merging of some of the closest-spaced spectral lines (missing right-most fringes in of FIG. 9B), and they cannot be detected by the automated image-processing software.

Figure 10:
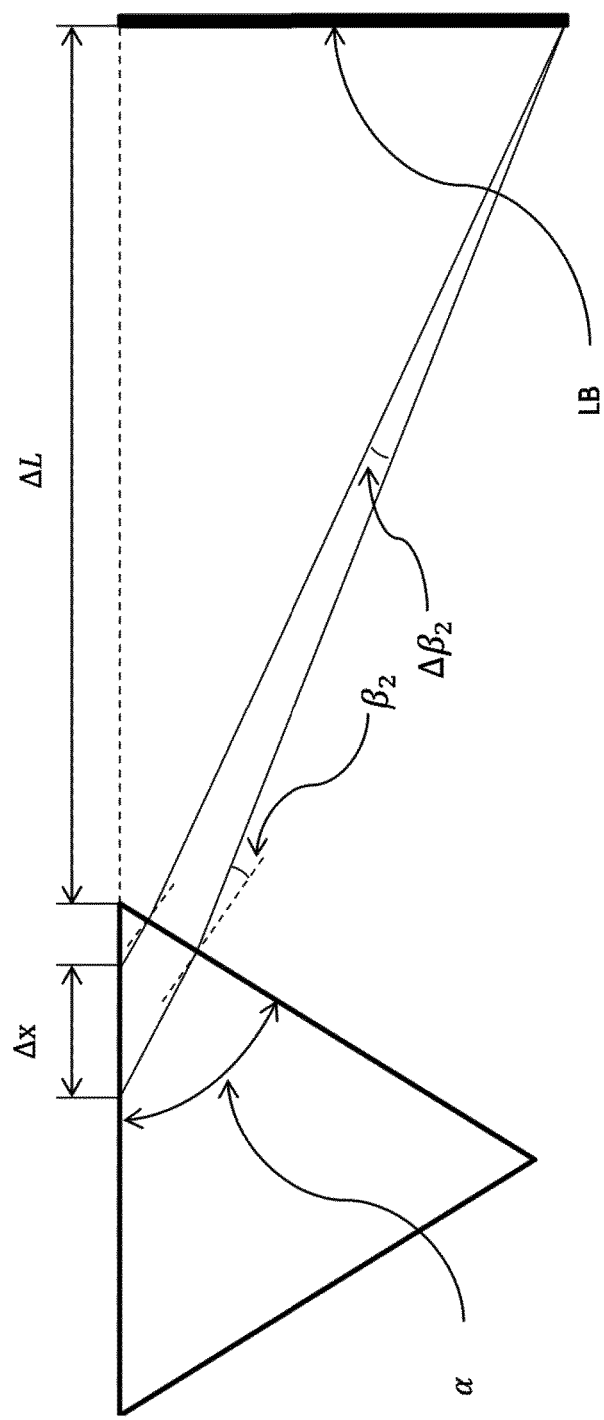
FIG. 10 is a diagram showing how placing a light block a significant distance from the prism can be utilized to provide a difference in the effective interaction length between the two ends of the measured effective index range.

In a related embodiment, a relatively large distance between the light block and the prism is utilized to enable effective interaction length of the measurement that varies with the effective index of the modes that are measured. A diagram showing how placing a light block LB a significant distance ΔL from the prism can be used to provide a difference Δx in the effective interaction length between the two ends of the measured effective index range $\Delta n_{eff}$, with corresponding prism exit angle range $\Delta\beta_2$ is shown in FIG. 10. In this example, the light block is placed on the exit side of the prism and in the arm of the detector. In particular, an index profile having a steep shallow region near the surface with rapidly decreasing index $$\left(\left|\frac{\lambda}{n}\frac{dn}{dz}\right| > 0.0004\right),$$

followed by a deep region of slowly decreasing index (penetrating >200λ/n from the surface, and having normalized slope $$\left|\frac{\lambda}{n}\frac{dn}{dz}\right| \leq 0.00007),$$

requires light blocking for improving the contrast of the low-order modes confined in the shallow steep region. At the same time, significant interaction length is required to be able to resolve the densely spaced highest-order modes propagating deep in the region of slowly decreasing index.

In one non-limiting example, the exit angle $\beta_2$ of light rays corresponding to effective indices of modes of the spectrum, measured with respect to the normal to the exit facet of the prism, is significantly smaller than 1 rad, and the range of exit angles corresponding to the entire spectrum of effective indices of the guided modes is $\Delta\beta_2$. In this instance, the light block of appropriate blocking height H that is placed a distance $\Delta L$ from the closest edge of the prism can impart a difference $\Delta x$ in effective interaction length between the lowest and the highest order modes, such that $$\Delta x \approx \frac{\Delta L}{\sin(\alpha - \beta_z)\cos\alpha} \Delta \beta_2.$$

For example, a prism with refractive index of 1.72 and base angle $\alpha+60°$, a double-ion-exchanged region with maximum index of 1.505 and minimum index of 1.492 has $\Delta\beta_2 \approx 20$ rad, and negligible $\beta_2$ compared to $\alpha$, such that $$\Delta x \approx \frac{0.025}{\sin\alpha\cos\alpha} \Delta L \approx 0.06 \Delta L.$$

The above equations provides a means of controlling the difference in effective coupling length over the breadth of effective index spectrum, to mitigate the need of trade-off between precision of the CS measurement and the systematic error of DOL measurement due to the inability to resolve high-order modes.

Figure 11:
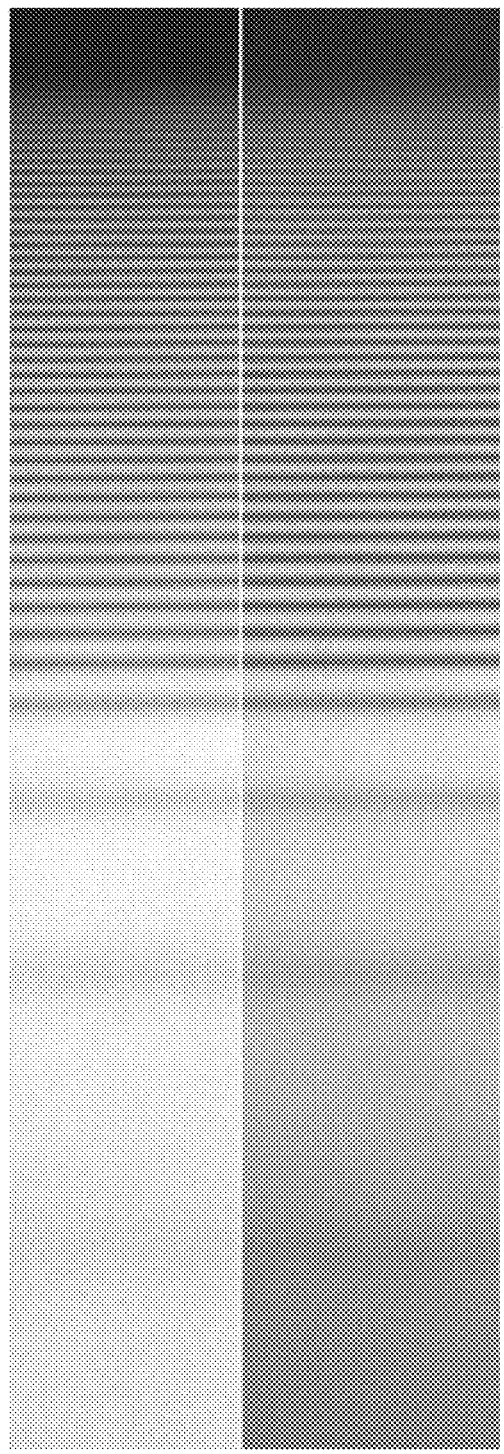
FIG. 11 is a photograph showing simultaneous improvement contrast for the low-order modes, and retention of ability to detect all modes of the double-ion-exchanged sample of FIGS. 9A and 9B.

Simultaneous improvement of contrast for the low-order modes, and retention of ability to detect all modes of the double-ion-exchanged sample of FIGS. 9A and 9B is shown in FIG. 11. The top image in FIG. 11 shows the TM mode spectrum obtained without light blocking. The bottom image in FIG. 11 shows the TM mode spectrum captured with the help of a light block LB placed a distance $\Delta L=82$ mm from the closer prism edge and having a total height of about 46 mm measured from the prism horizontal coupling facet (see FIG. 10 schematic). The distant light block increased the contrast for the low-order modes, without broadening of the highest-order coupling resonances (rightmost fringes in FIG. 11).

The improvement of contrast is achieved without loss of DOL accuracy (bottom image of FIG. 11) by placing a light block of 46 mm height at a distance of 80 mm from the prism edge. The height of the light block is calculated by calculating the exit angle of the ray corresponding to the lowest effective index, then accounting for the prism shape:

$$H = \Delta L \tan\left(\frac{\pi}{2} - \alpha - \beta_2(n_{sub})\right)$$

where $n_{sub}$ is the substrate index, chosen here to represent approximately the lowest effective index of the entire mode spectrum. The position and/or height of the light block may need to be adjusted slightly upon placement in order to obtain the best balance between uniformity of illumination, and contrast for the lowest-order modes.

While typical embodiments have been set forth for the purpose of illustration, the foregoing description should not be deemed to be a limitation on the scope of the disclosure or appended claims. Accordingly, various modifications, adaptations, and alternatives may occur to one skilled in the art without departing from the spirit and scope of the present disclosure or appended claims.

The invention claimed is:

1. A method of measuring waveguide mode spectra, the method comprising:

forming a coupling interface between a coupling surface of a prism and a surface of a waveguide, the waveguide having a surface region of decreasing index with normalized slope $$\left|\frac{\lambda}{n}\frac{dn}{dz}\right| > 0.0004,$$

where $n=n(z)$ is a refractive index profile of the waveguide as a function of a distance z into the waveguide from the waveguide surface and $\lambda$ is a measurement wavelength of a light beam from a light source, the surface region extending from a surface into the waveguide sample, and the prism having an input surface and an output surface;

disposing an opaque light-blocking element spaced apart from both the input surface and the output surface in a portion of a path of the light beam emanating from the light source, the portion being closest to a plane of contact between the coupling surface and the waveguide sample;

at least one of:

blocking at least a portion of the light beam with the opaque light-blocking, element, wherein the portion of the light beam is prevented from reaching a portion of the coupling surface along the path of the light beam; and blocking a first portion of light reflected from the coupling interface with the opaque light-blocking element, wherein the first portion is prevented from reaching a detector;

allowing a second portion of light reflected from the coupling interface to reach the detector; and detecting the second portion with the detector at a position corresponding to as lowest-order mode, and is less than or equal to 7 times the maximum possible effective coupling length of the lowest-order mode or 7 mm, whichever is less.

2. The method of claim 1, wherein the position corresponding to the lowest-order mode is less than or equal to 5 times the maximum effective coupling length.

3. The method of claim 2, wherein the at least one light-blocking element is located within 30 mm of an edge of the prism.

4. The method of claim 2, wherein the at least one light-blocking element is located within 7 mm of an edge of the prism.

5. The method of claim 2, wherein the waveguide further includes a deep region of decreasing index, the deep region penetrating to a depth of at least $170\lambda/n$ from the surface of the waveguide, and having normalized slope $$\left|\frac{\lambda}{n}\frac{dn}{dz}\right| < 0.00007.$$

6. The method of claim 5, wherein the depth of the deep region is at least $200\lambda/n$.

7. The method of claim 6, wherein at the least one light-blocking element is located at least 30 mm from a plurality of edges of the prism, and provides a substantial difference in illuminated interaction length or detected interaction length between the lowest-order mode and the highest-order mode.

8. The method of claim 7, wherein the light-blocking element is located less than or equal to 100 mm from each of the edges of the prism.

9. A method of measuring waveguide mode spectra, the method comprising:
forming a coupling interface between a coupling surface of a prism and a surface of a waveguide, the waveguide having a surface region of decreasing index with normalized slope $$\left|\frac{\lambda}{n}\frac{dn}{dz}\right| > 0.0004,$$

where $n=n(z)$ is a refractive index profile of the waveguide as a function of a distance z into the waveguide from the waveguide surface and $\lambda$ is a measurement wavelength of a light beam from a light source, the surface region extending from a surface into the waveguide sample, and the prism having an input surface and an output surface;
disposing an opaque light-blocking element spaced apart from both the input surface and the output surface in a portion of a path of the light beam emanating from the light source, the portion being closest to a plane of contact between the coupling surface and the waveguide sample, wherein the light-blocking element has a transmission, the transmission being a variable function of distance from the plane of contact with the transmission increasing as the distance from the plane of contact increases, and wherein the light-blocking element having the variable transmission is not a circular aperture;
at least one of:
blocking at least a portion of the light beam with the opaque light-blocking element, wherein the portion of the light beam is prevented from reaching a portion of the coupling surface along the path of the light beam; and
blocking a first portion of light reflected from the coupling interface with the opaque light-blocking element, wherein the first portion is prevented from reaching a detector;
allowing a second portion of light reflected from the coupling, interface to reach the detector; and
detecting the second port at with the detector at a position corresponding to a lowest-order mode, and is less than or equal to 7 times the maximum possible effective coupling length of the lowest-order mode or 7 mm, whichever is less.

10. The method of claim 9, wherein the light-blocking element is a plate having spatially varying absorption.

11. The method of claim 9, wherein the light-blocking element has a shape with more open space near a first side that is distal from the prism-sample coupling plane.

12. The method of claim 11, wherein the light-blocking element is made of essentially opaque material.

13. The method of claim 11, wherein the variation in open space from the first side to the prism-sample coupling, plane is achieved by a V-shaped cutout.

14. The method of claim 13, wherein of the V-shaped cutout forms an angle $\gamma$ of between about 30 degrees and about 50 degrees.

15. The method of claim 9, wherein the light-blocking element is positioned up to 100 mm from at least one edge of the prism.

16. The method of claim 9, wherein the light-blocking element is positioned up to 10 mm from at least one edge of the prism.

17. The method of claim 9, wherein light-blocking elements are disposed or both the input side and the output side of the prism.

18. The method of claim 9, wherein the light-blocking element having the transmission that is a variable function of distance is disposed on one side of the prism and in the optical path, and a rectangular light-blocking element having spatially non-varying transmission is disposed on an opposite side of the prism and in the optical path.

* * * * *